(12) United States Patent
Chandolia et al.

(10) Patent No.: US 12,125,200 B2
(45) Date of Patent: Oct. 22, 2024

(54) METHODS, DEVICES, AND SYSTEMS FOR DETERMINING PRESENCE OF APPENDICITIS

(71) Applicant: Siemens Healthcare GmbH, Erlangen (DE)

(72) Inventors: Hemant Chandolia, Bangalore (IN); Muniraju M, Bengaluru (IN)

(73) Assignee: Siemens Healthineers AG, Forchheim (DE)

( * ) Notice: Subject to any disclaimer, the term of this patent is extended or adjusted under 35 U.S.C. 154(b) by 355 days.

(21) Appl. No.: 17/588,907

(22) Filed: Jan. 31, 2022

(65) Prior Publication Data

US 2022/0254012 A1 Aug. 11, 2022

(30) Foreign Application Priority Data

Feb. 9, 2021 (EP) .................................... 21155982

(51) Int. Cl.
*G06T 7/00* (2017.01)
*G06N 20/00* (2019.01)
*G16H 30/20* (2018.01)
*G16H 50/20* (2018.01)

(52) U.S. Cl.
CPC .......... *G06T 7/0012* (2013.01); *G06N 20/00* (2019.01); *G16H 30/20* (2018.01); *G16H 50/20* (2018.01)

(58) Field of Classification Search
CPC ........ G06T 7/0012; G06T 2207/30004; G16H 30/20; G16H 50/20; G06N 20/00
See application file for complete search history.

(56) References Cited

U.S. PATENT DOCUMENTS 11,253,324 B1 * 2/2022 Bu .......................... G06T 7/143
2022/0401062 A1 * 12/2022 Naidu .................... A61B 8/085

FOREIGN PATENT DOCUMENTS

CN 110648739 A 1/2020

OTHER PUBLICATIONS

Abdullah, Walid, et al. "Reinforcement Learning-based Automatic Diagnosis of Acute Appendicitis in Abdominal CT." arXiv e-prints (2019): 1-9.

(Continued)

*Primary Examiner* — Daniel G Mariam
(74) *Attorney, Agent, or Firm* — Lempia Summerfield Katz LLC

(57) ABSTRACT

Methods, devices, and systems for determining a presence of appendicitis are provided. In one aspect, a method includes receiving a medical image associated with the patient. Further, the method includes determining, using at least one trained machine learning model, an anatomical position of the appendix in the medical image. Additionally, the method includes determining, using the at least one trained machine learning model, a dimension associated with the appendix in the medical image. The method also includes identifying if the dimension associated with the appendix is above a pre-defined threshold. Furthermore, the method includes generating a notification on an output unit if the dimension associated with the appendix is above the pre-defined threshold, wherein dimension associated with the appendix being above the pre-defined threshold indicates presence of appendicitis in the patient.

13 Claims, 7 Drawing Sheets

(56) References Cited

OTHER PUBLICATIONS

Awais, Muhammad, et al. "Accuracy and reliability of tablet computer as an imaging console for detection of radiological signs of acute appendicitis using PACS workstation as reference standard." Abdominal Radiology 43.5 (2018): 1254-1261.

Martin, M., et al. "Inflammatory appendix mass in patients with acute appendicitis: CT diagnosis and clinical relevance." Emergency radiology 22.1 (2015): 7-12.

McBee, Morgan P., et al. "Deep learning in radiology." Academic radiology 25.11 (2018): 1472-1480.

* cited by examiner

METHODS, DEVICES, AND SYSTEMS FOR DETERMINING PRESENCE OF APPENDICITIS

The present patent document claims the benefit of European Patent Application No. 21155982.8, filed Feb. 9, 2021, which is hereby incorporated by reference in its entirety.

FIELD OF TECHNOLOGY

The present disclosure relates to methods, devices, and systems for processing medical images. In particular, the disclosure relates to methods, devices, and systems for determining a presence of appendicitis in a patient.

BACKGROUND

Appendicitis is inflammation of appendix which is a tube-like structure attached to a posteromedial end of a large intestine of a patient. Appendicitis may cause pain in lower abdominal area along with nausea and other discomforting symptoms. If left untreated, the appendix may burst and result in infecting abdominal cavity of the patient. The appendix is usually located in the lower right quadrant of the abdomen. The base of the appendix is located 2 cm beneath the ileocecal valve that separates the large intestine from the small intestine. The human appendix averages 9 cm in length but may range from 5 cm to 35 cm. The diameter of the appendix averages at 6 mm. Therefore, a diameter greater than 6 mm indicates an inflamed appendix. The appendix may lie in different positions in the human body. For example, the anatomical position of the appendix may be anterior, retrocecal, post-ileal, paracecal, posterior, subcecal, pelvic, or promontoric. Current methods of identifying the presence of appendicitis in a patient includes performing a medical scan of abdomen and pelvic region of the patient, and manual identification of the orientation and dimension of the appendix. Therefore, diagnosis of appendicitis is dependent on the expertise of physicians and may be prone to errors.

Currently, there is no way in which the presence of appendicitis in a patient may be automatically identified. Therefore, there is a need for a method and system which enables effective determination of presence of appendicitis in a patient, that is accurate and fast.

SUMMARY

The object of the disclosure is therefore to provide a method, device, and system that enables effective determination of presence of appendicitis in a patient.

The scope of the present disclosure is defined solely by the appended claims and is not affected to any degree by the statements within this summary. The present embodiments may obviate one or more of the drawbacks or limitations in the related art.

The disclosure achieves the object by a method of determining a presence of appendicitis in a patient. The method includes receiving a medical image associated with the patient. The medical image may be received from a medical imaging device. The medical imaging device may include, but is not limited to, a computed tomography device, an X-ray imaging device, a magnetic resonance imaging device, an ultrasound imaging system, etc. The medical image may be two-dimensional and/or related to an imaging plane. Further, the medical image data may be three-dimensional and/or related to a volume. The imaging plane and/or the volume may be a part of a patient body. The imaging plane and/or the volume may include one or more objects associated with a patient. The objects may be one or more body parts associated with the patient that may have been imaged. The objects may include, but are not be limited to, one or more imaged organs, tissues, or skeletal information associated with the patient. For example, the object may be the appendix of the patient. The medical image may be in the form of an array of voxels or voxels. Such arrays of voxels or voxels may be representative of intensity, absorption, or other parameter as a function of three-dimensional position, and may be obtained by suitable processing of measurement signals obtained by one or more of the above-mentioned medical imaging devices. In particular, the medical image may include information associated with the appendix of the patient.

The method further includes determining an anatomical position of the appendix in the medical image. The anatomical position may reflect an orientation of the appendix in the body of the patient. In an embodiment, the anatomical position of the appendix is determined using a trained machine learning model. The appendix may have one of the following orientations in the patient's body. For example, the orientation may be anterior, retrocecal, post-ileal, paracecal, posterior, subcecal, pelvic, or promontoric. The trained machine learning model may be configured to analyze the medical image of the appendix to determine the anatomical position of the appendix in the medical image. Further, the method includes determining a dimension associated with the appendix in the medical image. The trained machine learning model may be further configured to determine the dimension associated with the appendix in the medical image. The dimension may include a length/height, a diameter and a width associated with the appendix.

The method includes identifying if the dimension associated with the appendix is above a pre-defined threshold. The pre-defined threshold associated with the appendix may be a set of standard dimensions associated with an appendix which is not inflamed. In an embodiment, the pre-defined threshold associated with the appendix includes a width of the appendix to be in a range of 3 mm to 5 mm, a height of the appendix to be in a range of 80 mm to 100 mm, and a diameter of the appendix to be in a range of 8 mm to 12 mm. The method further includes generating a notification on an output unit when the dimension associated with the appendix is above the pre-defined threshold. If the dimension of the appendix is above the pre-defined threshold, it may be an indication of presence of appendicitis in the patient. For example, the dimension of the appendix may be above the pre-defined threshold in case of an inflammation. Advantageously, the method enables effective identification of presence of appendicitis in a patient. Therefore, manual effort of analyzing the medical images is eliminated.

According to an embodiment, determining the anatomical position of the appendix in the medical image using the at least one trained machine learning model includes analyzing the medical image to obtain one or more pixel information. The one or more pixel information may include pixels associated with the appendix in the medical image and pixel values associated with the pixels. The one or more pixel information enables effective identification of the appendix in the medical image. Using the one or more pixel information, one or more edges of the appendix in the medical image may be effectively identified. The method further includes identifying at least one pattern from the one or more pixel information. For example, the pattern may represent information related to anatomical position of the appendix in the medical image. Depending on the orientation of the appendix in the patient's body, the anatomical position of the appendix depicted in the medical image may vary. Therefore, the one or more pixel information associated with the appendix may be used to identify the anatomical position of the appendix in the medical image. The method includes determining the anatomical position of the appendix based on the identified at least one pattern. The pattern may indicate the orientation of the appendix in the patient's body. Therefore, the anatomical position of the appendix may be accurately determined based on the identified pattern. Advantageously, the trained machine learning model enables accurate identification of anatomical position of the appendix. Therefore, the need for expertise of a physician to manually identify the position of the appendix is avoided.

According to an embodiment, determining the dimension associated with the appendix using the at least one trained machine learning algorithm includes analyzing the medical image to obtain the one or more pixel information associated with the appendix in the medical image. From the pixel information, one or more pixel values may be identified which may be associated with the appendix. For example, based on the pixel values, one or more edges of the appendix in the medical image may be identified. If the one or more edges of the appendix are traced, the dimension associated with the appendix in the medical image may be determined. For example, the length of the appendix may be a longest distance between two points on lying on opposite edges of the appendix in the medical image. For example, the diameter of the appendix may be a distance between two parallel edges of the appendix that passes through a center of the appendix. Advantageously, the machine learning model enables accurate calculation of dimension of the appendix in the medical image. Therefore, this enables effective determination of presence of appendicitis in the patient.

According to an embodiment, generating a notification on the output unit may include generating an alert on a user interface of the output unit. The alert may include information related to anatomical position and dimension associated with the appendix in the medical image. Alternatively, a contour associated with the appendix in the medical image may be highlighted to indicate that the dimension associated with the appendix is above the pre-defined threshold. In a further embodiment, the contour of the appendix may be highlighted with different colors, wherein a first color may indicate that the dimension associated with the appendix is within/below the pre-defined threshold and the second color may indicate that the dimension associated with the appendix is above the pre-defined threshold. Advantageously, the notification enables a physician to take accurate steps in a medical treatment to be provided to the patient.

The object of the disclosure is also achieved by a method of training a machine learning model for determining presence of appendicitis in a patient. The method includes receiving a medical image associated with the patient. The medical image may include an appendix of the patient. In an embodiment, the medical image may be received from a medical imaging unit or from a medical database including a plurality of medical images. The method further includes receiving a machine learning model configured to determine presence of appendicitis in the patient. The machine learning model may be configured to analyze the medical image to determine an anatomical position and dimension associated with the appendix in the medical image. The method further includes comparing the determined anatomical position and the dimension with a pre-labelled set of medical images. The pre-labelled set of medical images may include a plurality of labels which may indicate an anatomical position of the appendix in the medical image. The labels may also include information related to dimension of the appendix in the medical images.

The method further includes adjusting the machine learning model based on an outcome of the comparison. For example, if the comparison between the anatomical position and dimensions determined by the machine learning model and the anatomical position and dimensions of the appendix from the pre-labelled medical images yields a difference, the machine learning model is adjusted based on the pre-labelled medical images. Alternatively, the identified difference may be provided to a user on an output unit for further processing. Further, based on the input obtained from the user, the machine learning model may be adjusted. Advantageously, training of the machine learning model improves the accuracy of the machine learning model. Therefore, determination of a presence of appendicitis in the patient is improved and optimized.

According to a further embodiment, the method includes obtaining one or more medical images associated with appendixes of a plurality of patients. Such one or more medical images may represent multiple anatomical positions of the appendixes and different dimensions associated with the appendixes. In an embodiment, the machine learning model determines the anatomical position and dimensions associated with the appendix of the patient based on the one or more medical images. In a yet another embodiment, the one or more medical images may include images of appendixes which have dimensions within a pre-defined threshold of dimensions for appendix and also images of appendixes which have dimensions above the pre-defined threshold.

In an embodiment, the machine learning model is a convolutional neural network (CNN). The CNN may have a plurality of layers with filters, including a pooling layer and a fully connected layer. The plurality of layers include a first layer called a convolutional layer which extracts features from the medical image including the appendix. Convolutional layer enables preservation of relationship between pixels based on the extracted features. The filters in the CNN enable accurate identification of edges of the appendix in the medical image. The plurality of the layers may also include a batch normalization layer configured to normalize pixel values and increase a speed of computation of the CNN. The pooling layer performs down sampling of features and retains pixel information necessary for further analysis. The medical image is then fed to the fully connected layer where the features are converted/flattened into vectors. The fully connected layers perform high-level reasoning in the CNN. An activation function, for example, softmax activation function classifies output of the CNN. The classification of the medical image may be, for example, as a medical image indicating appendicitis or not indicating appendicitis.

The object of the disclosure is also achieved by a medical imaging device for determining presence of appendicitis in a patient. The device includes one or more processing units, a scanner unit configured to capture one or more medical images, and a memory coupled to the one or more processing units. The memory includes an appendicitis determining module configured to perform the method acts as described above, using at least one trained machine learning model.

The disclosure relates in another aspect to a system for determining presence of appendicitis in a patient. According to an embodiment, the system includes one or more one or more servers and a medical imaging device coupled to the one or more servers. The one or more servers include instructions, which when executed causes the one or more servers to perform the method acts as described above, using at least one machine learning model.

The disclosure relates in one aspect to a non-transitory computer-readable storage medium storing machine-readable instructions therein, that when executed by a processor, causes the processor to receive a medical image associated with the patient, wherein the medical image includes an appendix of the patient. Further, the instructions cause the processor to determine, using at least one trained machine learning model, an anatomical position of the appendix in the medical image and determine, using the at least one trained machine learning model, a dimension associated with the appendix in the medical image. Additionally, the instructions cause the processor to identify, using the at least one trained machine learning model, if the dimension associated with the appendix is above a pre-defined threshold and generate a notification on an output unit when the dimension associated with the appendix is above the pre-defined threshold, wherein dimension associated with the appendix being above the pre-defined threshold indicates presence of appendicitis in the patient.

BRIEF DESCRIPTION OF THE DRAWINGS

The present disclosure is further described hereinafter with reference to illustrated embodiments shown in the accompanying drawings, in which.

DETAILED DESCRIPTION

Figure 1:
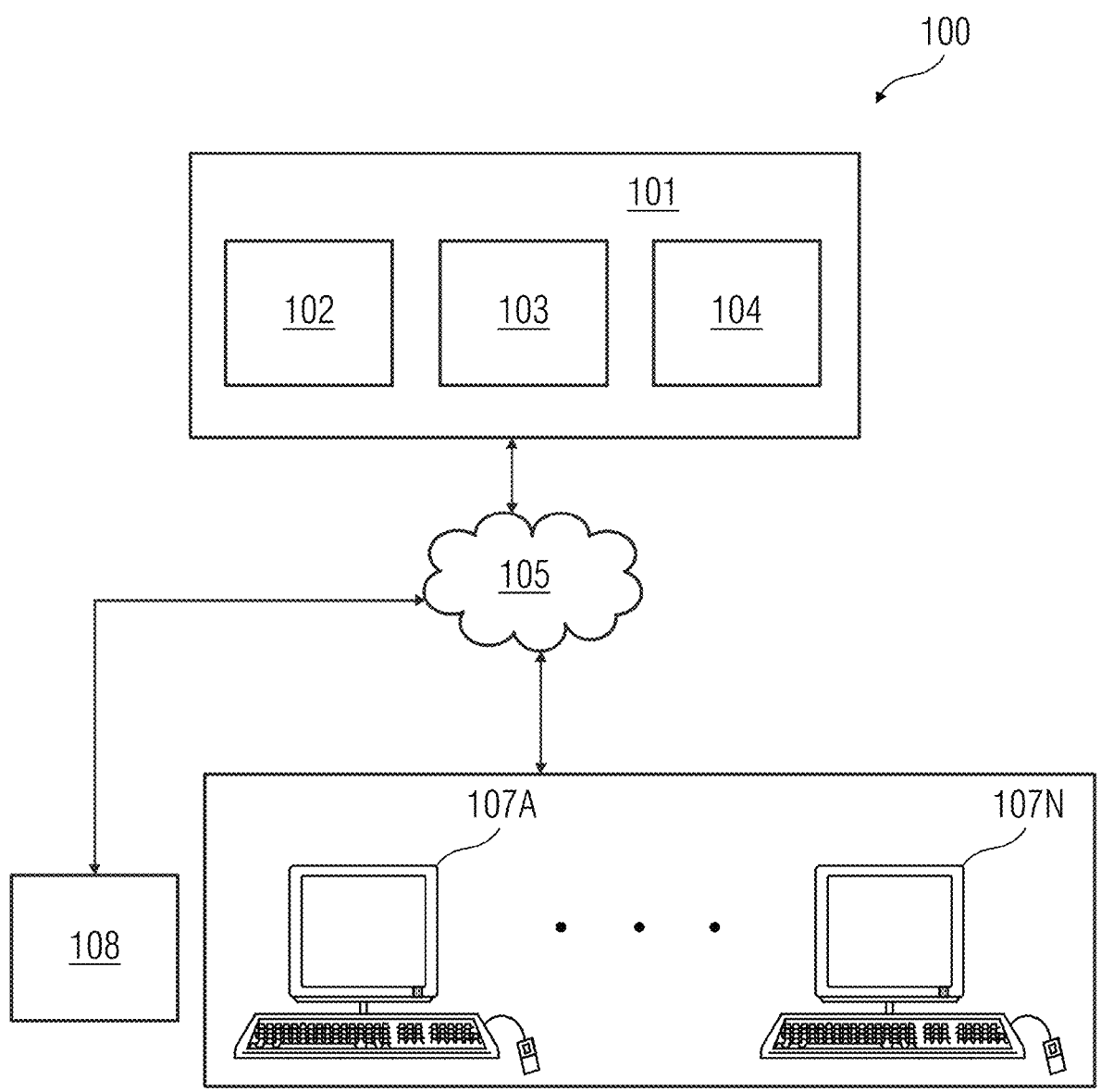
FIG. 1 illustrates a block diagram of a client-server architecture which provides a geometric modeling of components representing different parts of a real-world object, according to an embodiment.

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

In the following, the solution is described with respect to the claimed providing systems as well as with respect to the claimed methods. Features, advantages, or alternative embodiments herein may be assigned to the other claimed objects and vice versa. In other words, claims for the providing systems may be improved with features described or claimed in the context of the methods. In this case, the functional features of the method are embodied by objective units of the providing system.

Furthermore, in the following the solution is described with respect to methods and systems for determining a presence of appendicitis in a patient as well as with respect to methods and systems for training a machine learning model for determining a presence of appendicitis in a patient. Features, advantages, or alternative embodiments herein may be assigned to the other claimed objects and vice versa. In other words, claims for methods and systems for training the machine learning model for determining a presence of appendicitis in a patient may be improved with features described or claimed in context of the methods and systems for determining a presence of appendicitis in a patient, and vice versa. In particular, the trained machine learning model of the methods and systems for determining a presence of appendicitis in a patient may be adapted by the methods and systems for training the machine learning model for determining a presence of appendicitis in a patient. Furthermore, the input data may include advantageous features and embodiments of the training input data, and vice versa. Furthermore, the output data may include advantageous features and embodiments of the output training data, and vice versa.

FIG. 1 provides an illustration of a block diagram of a client-server architecture that is a geometric modelling of components representing different parts of real-world objects, according to an embodiment. The client-server architecture 100 includes a server 101 and a plurality of client devices 107A-N. Each device of the client devices 107A-N is connected to the server 101 via a network 105, for example, local area network (LAN), wide area network (WAN), WiFi, etc. In one embodiment, the server 101 is deployed in a cloud computing environment. As used herein, "cloud computing environment" refers to a processing environment including configurable computing physical and logical resources, for example, networks, servers, storage, applications, services, etc., and data distributed over the network 105, for example, the internet. The cloud computing environment provides on-demand network access to a shared pool of the configurable computing physical and logical resources. The server 101 may include a medical database 102 that includes medical images and associated medical data related to a plurality of patients that is maintained by a healthcare service provider. The server 101 may include an appendicitis determination module 103 that is configured to determine a presence of appendicitis in a patient. Additionally, the server 101 may include a network interface 104 for communicating with the client device 107A-N via the network 105.

The client device 107A-N are user devices, used by users, (e.g., medical personnel such as a radiologist, pathologist, physician, etc.). In an embodiment, the user device 107A-N may be used by the user to receive data associated with the patient. The data may be accessed by the user via a graphical user interface of an end user web application on the user device 107A-N. In another embodiment, a request may be sent to the server 101 to access the data associated with the patient via the network 105. An imaging unit 108 may be connected to the server 101 through the network 105. The unit 108 may be a medical imaging unit 108 capable of acquiring a plurality of medical images. The medical imaging unit 108 may be, for example, a scanner unit such as a computed tomography imaging unit, an X-ray imaging unit, a magnetic resonance imaging unit, an ultrasound imaging unit, etc.

Figure 2:
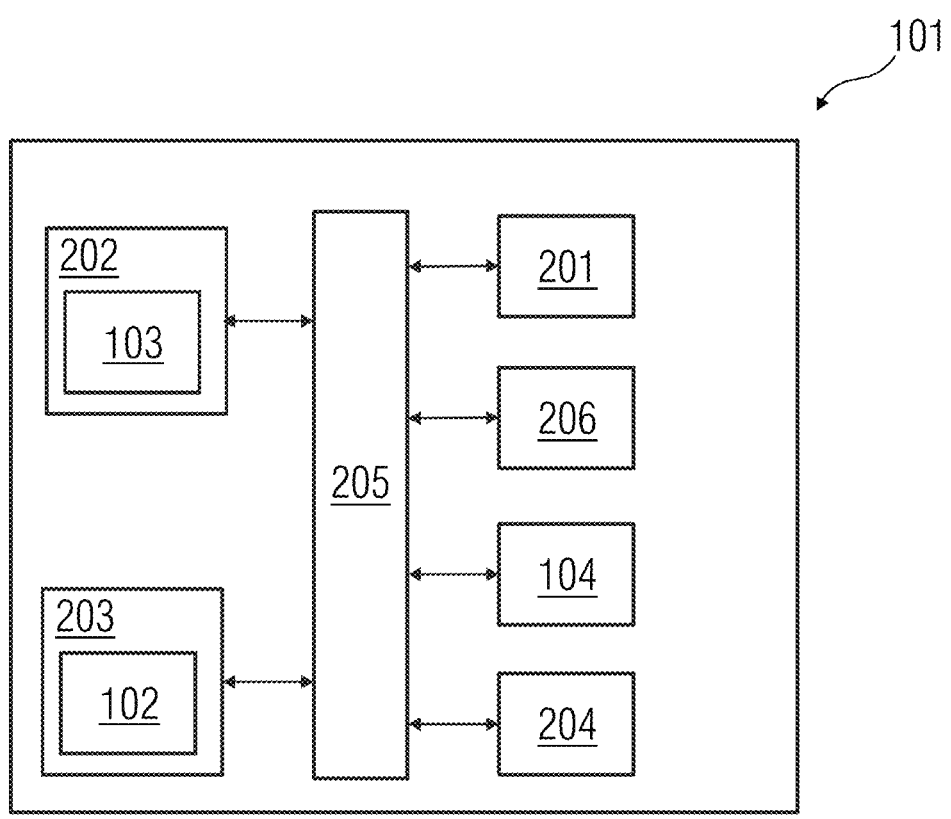
FIG. 2 illustrates a block diagram of a data processing system in which an embodiment for determining presence of appendicitis in a patient may be implemented.

FIG. 2 is a block diagram of a data processing system 101 in which an embodiment may be implemented, for example, as a system 101 for determining a presence of appendicitis in a patient, configured to perform the processes as described therein. It is appreciated that the server 101 is an exemplary implementation of the system in FIG. 2. In FIG. 2, the data processing system 101 includes a processing unit 201, a memory 202, a storage unit 203, an input unit 204, an output unit 206, a bus 205, and a network interface 104.

The processing unit 201, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 201 may also include embedded controllers, such as generic or programmable logic devices or arrays, application specific integrated circuits, single-chip computers, and the like.

The memory 202 may be volatile memory and non-volatile memory. The memory 202 may be coupled for communication with the processing unit 201. The processing unit 201 may execute instructions and/or code stored in the memory 202. A variety of computer-readable storage media may be stored in and accessed from the memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 202 includes an appendicitis determination module 103 stored in the form of machine-readable instructions on any of the above-mentioned storage media and may be in communication to and executed by processor 201. When executed by the processor 201, the appendicitis determination module 103 causes the processor 201 to process a medical image to determine a presence of appendicitis in a patient. Method acts executed by the processor 201 to achieve the abovementioned functionality are elaborated upon in detail in FIGS. 3, 4, 5, and 6.

The storage unit 203 may be a non-transitory storage medium which stores a medical database 102. The medical database 102 is a repository of medical images and associated medical data sets related to one or more patients that is maintained by a healthcare service provider. The input unit 204 may include an input device such as keypad, touch-sensitive display, camera (such as a camera receiving gesture-based inputs), etc., capable of receiving input signal such as a medical image. The bus 205 acts as interconnect between the processor 201, the memory 202, the storage unit 203, the input unit 204, the output unit 206, and the network interface 104.

Those of ordinary skilled in the art will appreciate that the hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter also may be used in addition or in place of the hardware depicted. The depicted example is provided for the purpose of explanation only and is not meant to imply architectural limitations with respect to the present disclosure.

A data processing system 101 in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through a pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Washington may be employed if suitably modified. The operating system is modified or created in accordance with the present disclosure as described.

Disclosed embodiments provide systems and methods for processing medical images. In particular, the systems and methods may enable determination of presence of appendicitis in a patient.

Figure 3:
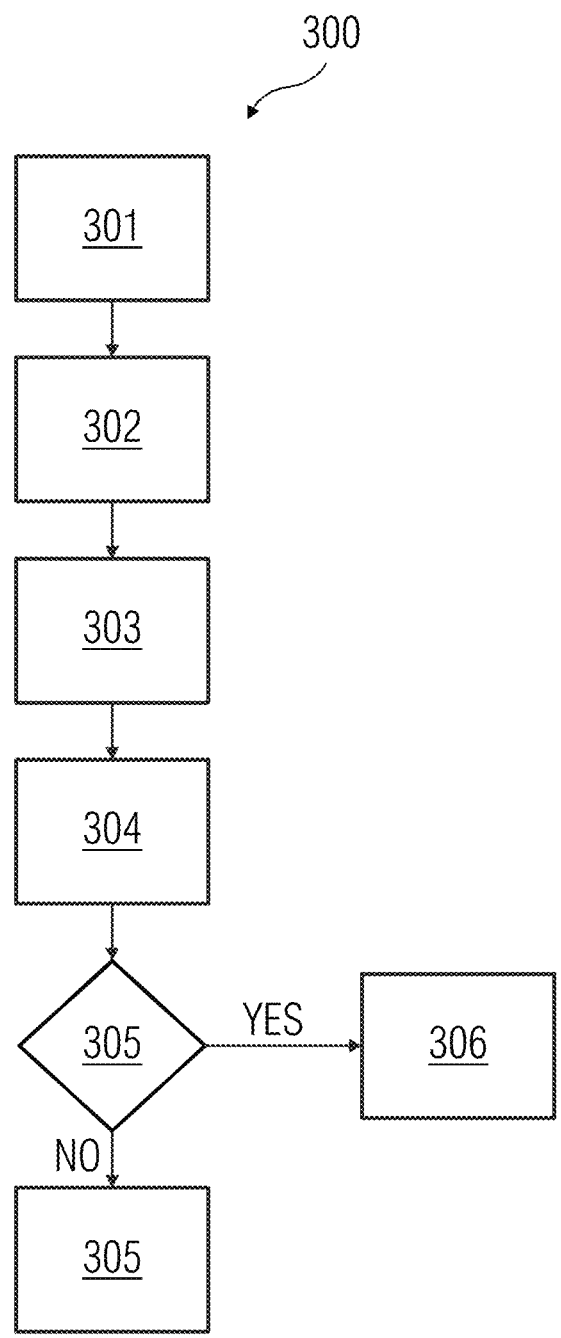
FIG. 3 illustrates a flowchart of a method of determining presence of appendicitis in a patient, according to an embodiment.

FIG. 3 illustrates a flowchart of a method 300 of determining a presence of appendicitis in a patient, according to an embodiment. At act 301, a medical image data associated with the appendix of the patient is received. The medical image may be received from a medical imaging unit such as an X-ray imaging unit, a computed tomography imaging unit, a magnetic resonance imaging unit, an ultrasound imaging unit, etc. Alternatively, the medical image may be received from the medical database 102. The medical image may include one or more objects associated with the patient. The objects may be one or more body parts associated with the patient. In the present embodiment, the imaged object includes the appendix of the patient. At act 302, an anatomical position of the appendix in the medical image is determined using a trained machine learning model. In an embodiment, the appendix may have an anatomical position which may be one of anterior, retrocecal, post-ileal, paracecal, posterior, subcecal, pelvic, and promontoric positions. Accurate identification of anatomical position of the appendix enables effective medical treatment for appendicitis. The trained machine learning model may be a convolutional neural network configured to analyze the medical image and determine the accurate anatomical position/orientation of the appendix in the medical image.

At act 303, a dimension associated with the appendix is determined by the at least one trained machine learning model. The dimensions of the appendix provide details on presence of appendicitis in the patient. For example, if the dimensions associated with the appendix is greater than a pre-defined threshold, it may be an indication of presence of appendicitis in the patient. At act 304, the determined dimensions of the appendix are compared with a pre-defined threshold. The pre-defined threshold may represent a standard set of dimensions associated with appendixes in human beings. For example, the pre-defined threshold associated with the appendix includes a width of the appendix to be in a range of 3 mm to 5 mm, a height of the appendix to be in a range of 80 mm to 100 mm, and a diameter of the appendix to be in a range of 8 mm to 12 mm.

At act 305, a determination is made if the dimension associated with the appendix in the medical image is above or within the pre-defined threshold. If the dimensions associated with the appendix is above the pre-defined threshold, at act 306, a notification is generated on the output unit indicating the presence of appendicitis in the patient. Alternatively, if the dimensions associated with the appendix is within the pre-defined threshold, a notification indicating absence of appendicitis in the patient may be generated on the output unit, at act 307. In an embodiment, the notification generated at act 306 and/or act 307 may include the medical image of the patient in which a contour associated with the appendix is highlighted. For example, if the dimensions associated with the appendix is above the pre-defined threshold, the contour of the appendix may be highlighted in a specific first color. Similarly, if the dimensions of the appendix are within the pre-defined threshold, the contour of the appendix may be highlighted with a second color, wherein the second color is different from the first color.

Figure 4:
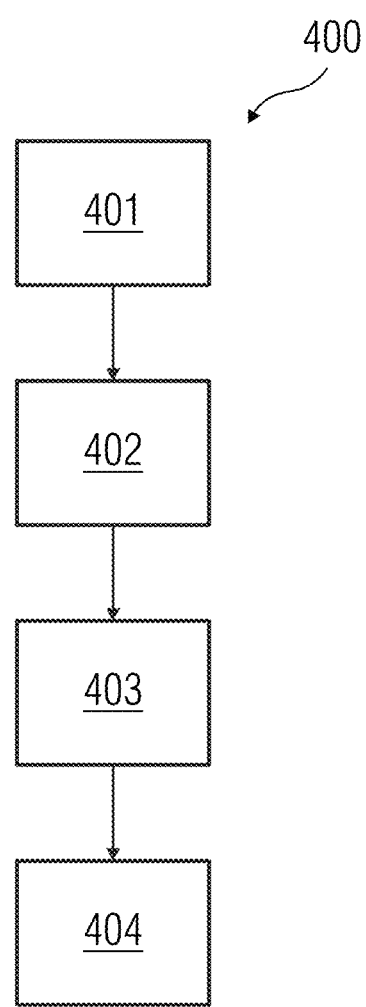
FIG. 4 illustrates a flowchart of a method of determining the anatomical position of the appendix in the medical image, according to an embodiment.

FIG. 4 illustrates a flowchart of a method 400 of determining the anatomical position of the appendix, according to an embodiment. At act 401, the medical image is analyzed to obtain one or more pixel information associated with the medical image. The pixel information may include, for example, one or more pixel values associated with the pixels in the medical image. The trained machine learning model may be a convolutional neural network (CNN). At act 402, the CNN may be trained to analyze the pixel information in the medical image to identify at least one pattern based on the pixel information. The pattern may be an indication of an anatomical structure of the appendix. In an embodiment, the CNN may be trained using a plurality of medical images including different anatomical positions of the appendix. The method acts describing how the CNN is trained is disclosed in FIG. 6. For example, the pixel information may be used to identify a contour associated with the appendix in the medical image. Based on the contour, the orientation of the appendix may be determined. In a further embodiment, at act 403, the determined pattern may be classified to identify which the orientation of the appendix in the medical image out of the plurality of orientations associated with the appendix. At act 404, the anatomical position of the appendix is identified based on the identified pattern.

Figure 5:
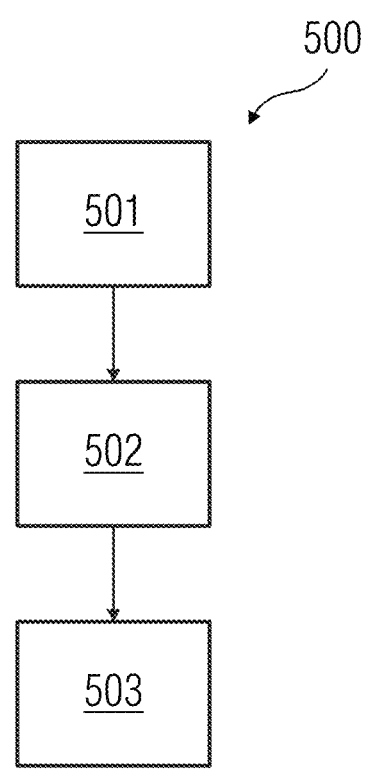
FIG. 5 illustrates a flowchart of a method of determining the dimension associated with the appendix, according to an embodiment.

FIG. 5 illustrates a method 500 of determining the dimension associated with the appendix in the medical image, using the trained machine learning model, according to an embodiment. At act 501, The medical image is analyzed to obtain the pixel information associated with the appendix. At act 502, the pixel information is used to identify one or pixel values associated with the appendix in the medical image. Based on the pixel values, the contour associated with the appendix may be determined. In particular, the contour may be identified using the CNN by detecting one or more edges associated with the appendix. Further, the dimensions of the appendix may be measured based on the contour of the appendix. For example, the length of the appendix may be a longest distance between two points on lying on opposite edges of the appendix in the medical image. For example, the diameter of the appendix may be a distance between two parallel edges of the appendix that passes through a center of the appendix. Therefore, at act 503, the dimension associated with the appendix is determined based on the one or more pixel values.

Figure 7:
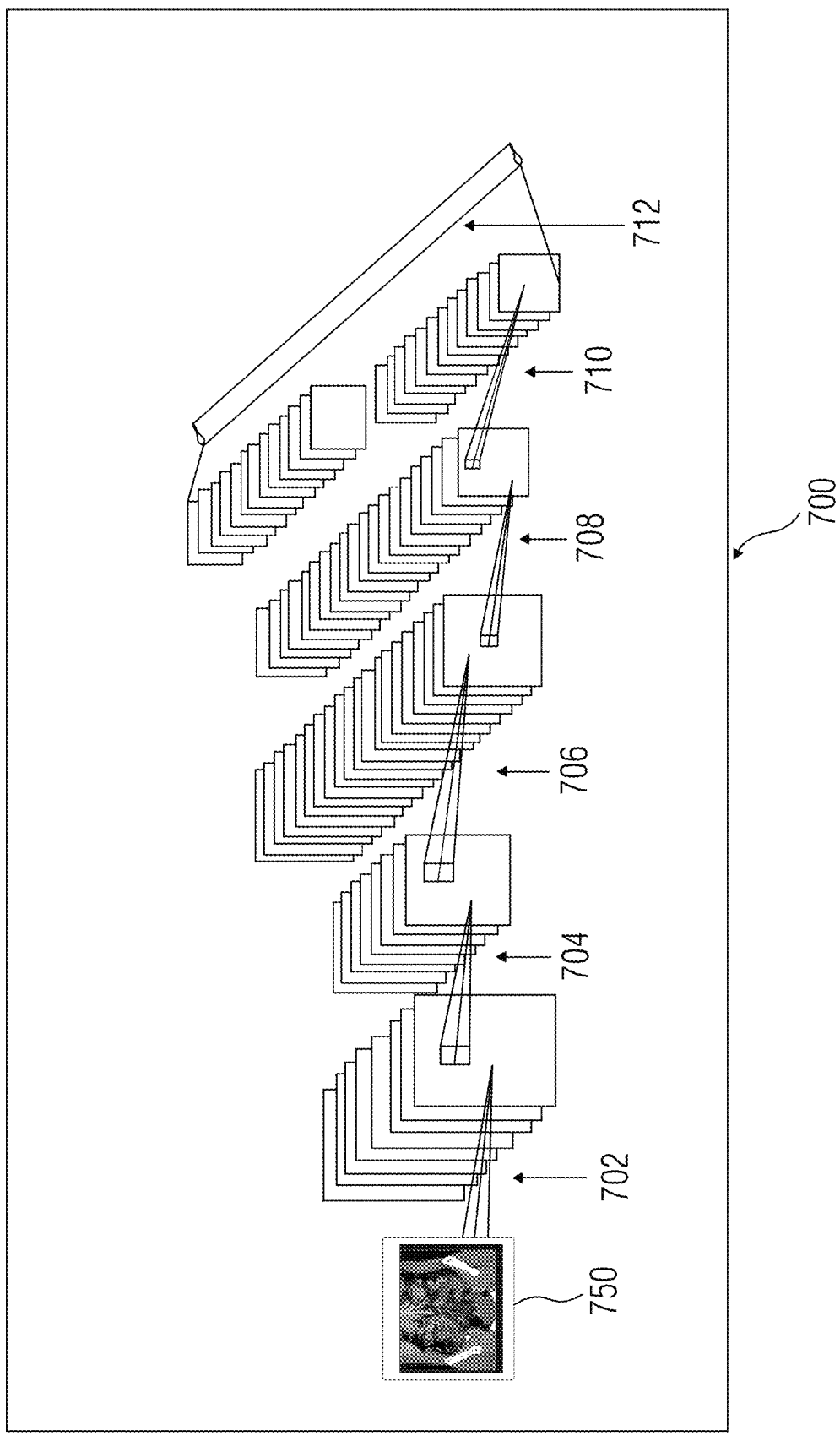
FIG. 7 illustrates a working of the machine learning model for determining the presence of appendicitis, according to an embodiment.

FIG. 7 illustrates a working of the machine learning model 700 for determining the presence of appendicitis, according to an embodiment. The system 100 uses neural networks to identify and extract pixel information from the one or more medical images. In the present embodiment, convolutional neural networks are used to identify and extract the pixel information associated with the medical image. In an embodiment, the medical image may be pre-processed before being processed by the CNN. For example, a portion of the medical image depicting only the appendix of the patient is identified. This may be done based on the contour of the appendix in the medical image. In a further embodiment, the portion of the medical image may be resized such that the image contains pixel information of type [W×H×D]. The pixel information may be normalized such that the pixel values associated with the medical image are in the range of 0-1.

As shown in the figure, the pre-processed medical image 750 is provided to an input layer of the CNN 700. The CNN 700 extracts relevant information from pixels of the medical image 750 and inputs the same into a fully connected neural network with an output layer 712 yielding medical image indicating a presence or absence of appendicitis in the patient. The CNN 700 is trained on a set of example medical images which may indicate presence of appendicitis, and which may not indicate presence of appendicitis. In an embodiment, approximately 70% of the medical images may be used for training of the machine learning model 700, approximately 15% of the medical images may be used for validation of the machine learning model 700, and approximately 15% of the medical images may be used for testing the machine learning model 700. The evaluation of the machine learning model 700 may be performed to determine an accuracy rate of the machine learning model 700.

In particular, the medical image 750 is represented as a two-dimensional array of pixel intensities for three array dimensions for feature maps including height and width. The medical image 750 is transformed through convolutional feature extraction layers 702 according to the following equation:

$$h_{l,i,j}^{(k)} = \emptyset((W_l^{(k)} * h_{l-1})_{ij} + b_l^{(k)})$$

where l denotes the layer index, k denotes the feature map index, $h_0$ corresponds to the image pixel array, $W_l^{(k)}$ and $b_l^{(k)}$ are the filters and biases, which correspond to the l-th layer and k-th feature map, learned from training examples, and Ø is an element wise activation function such as sigmoid(x) or max(0,x) (rectified linear unit, ReLU).

The CNN 700 includes a convolutional layer. The layers include a set of filters or kernels which have a small receptive field but extend through a full depth of the input volume. During a forward pass, each filter is convolved across the width and height of the input data [W×H×D] computing a dot product of entries of the filters and the input to generate a two-dimensional activation map of that filter. In an embodiment, the convolutional layer 702 includes 32 filters with a filter size of (7, 7) and stride of 1.

As shown in FIG. 7, pooling layers 704 and 708 are used subsequent to convolutional layers 702 and 706. The pooling layers 704 and 708 aggregate spatially local regions using a max-function, (e.g., the maximum value of the spatial local region is selected). For example, spatially local regions of size 2×2 may be aggregated using the max-function, (e.g., the maximum value of the 2×2 region is selected). Common aggregation functions are the maximum or average function, but other functions are possible. The pooling layers 704 and 708 perform down sampling of features and retain only the pixel information necessary for further analysis. The pooling layers 704 and 708 may have a stride of 4*4. Spatial dropouts with a dropout rate of 0.3 are introduced between consecutive convolutions. The CNN 700 further includes a fully connected layer 710 where high-level reasoning is performed. Neurons in the fully connected layer 710 have connections to all activations in the previous layers. The activations may therefore be computed as an affine transformation with matrix multiplication followed by a bias offset. Matrix of the medical image is then fed to the fully connected layer 710 where the features are converted/ flattened into vectors. An activation function, for example, softmax activation function classifies output of the CNN 700. The output layer 712 yields classification of the medical image as indicating a presence of appendicitis or not indicating a presence of appendicitis.

Figure 6:
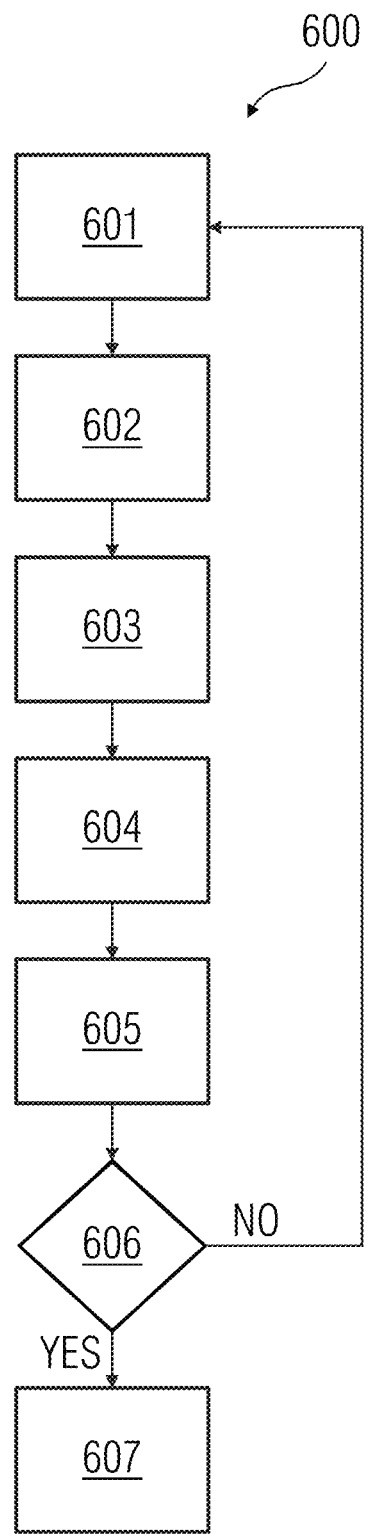
FIG. 6 illustrates a flowchart of a method of training a chine learning model for determining the presence of appendicitis in the patient, according to an embodiment.

FIG. 6 illustrates a flowchart of a method 600 of training a machine learning model 700 for determining the presence of appendicitis in the patient, according to an embodiment. At act 601, a medical image representing an appendix of a patient is received by a processing unit. The medical image may be received from the scanner unit 108 or from the medical database 102 which may include a plurality of medical images. At act 602, a machine learning model 700 is received by the processing unit. At act 603, the anatomical positions and dimensions associated with the appendix is determined by the machine learning model 700. The machine learning model 700 may be configured to process the medical image to identify one or more pixel information, based on which the anatomical position and the dimension associated with the appendix may be determined. For example, the machine learning model 700 may have a plurality of computational layers configured to process the one or more pixel information associated with the appendix in the medical image. At act 604, a set of pre-labelled medical images is received from the medical database 102. The pre-labelled set of medical images may include, for example, medical images which have labelled/annotated information related to anatomical position and dimension of the appendix. At act 605, the anatomical position and the dimension of the appendix determined by the machine learning model 700 is compared with a pre-labelled set of medical images. At act 606, a determination is made if there exists a difference between the anatomical position and dimension information determined by the machine learning model 700 and the anatomical position and dimension information present in the pre-labelled set of medical images. If a difference is identified, at act 607 the machine learning model 700 is adjusted according to the pre-labelled set of medical images. Alternatively, the output of the comparison may be displayed on the output unit to a user for decision making. Further, based on the decision of the user, the machine learning model 700 may be adjusted.

In a further embodiment, the machine learning model 700 may further be trained to learn from one or more medical images associated with appendix of a plurality of individuals/patients. Such one or more medical images may depict multiple anatomical positions and dimensions associated with the appendix. Therefore, the machine learning model 700 may determine the anatomical position and the dimension of the appendix associated with the patient based on the learnings from the one or more medical images associated with the plurality of individuals/patients.

An advantage of the disclosure is the method and system enable automatic identification of presence of appendicitis in the patient. Therefore, dependency on manual expertise for such determination is reduced. Furthermore, appendicitis may be diagnosed for all different anatomical positions of the appendix in a patient's body. Therefore, accuracy of the diagnosis is improved. Additionally, time taken for such diagnosis is reduced thereby enabling a faster treatment process.

The foregoing examples have been provided merely for the purpose of explanation and are in no way to be construed as limiting of the present disclosure. While the disclosure has been described with reference to various embodiments, it is understood that the words, which have been used herein, are words of description and illustration, rather than words of limitation. Further, although the disclosure has been described herein with reference to particular means, materials, and embodiments, the disclosure is not intended to be limited to the particulars disclosed herein; rather, the disclosure extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosure in its aspects.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A computer implemented method of determining a presence of appendicitis in a patient, the method comprising:
   receiving a medical image associated with the patient, wherein the medical image comprises an appendix of the patient;
   determining, using at least one trained machine learning model, an anatomical position of the appendix in the medical image;
   determining, using the at least one trained machine learning model, a dimension associated with the appendix in the medical image comprising: (1) analyzing the medical image to obtain pixel information associated with the appendix in the medical image; (2) identifying one or more pixel values from the pixel information associated with the appendix; (3) identifying one or more edges of the appendix based on the one or more pixel values; and (4) determining the dimension associated with the appendix from the identified one or more edges;
   identifying, using the at least one trained machine learning model, if the dimension associated with the appendix is above a pre-defined threshold; and
   generating a notification on an output unit when the dimension associated with the appendix is above the pre-defined threshold,
   wherein the dimension associated with the appendix being above the pre-defined threshold indicates the presence of appendicitis in the patient.

2. The method of claim 1, wherein the determining of the anatomical position of the appendix comprises:
   identifying at least one pattern from the pixel information, wherein the pattern represents anatomical positional information associated with the appendix; and
   determining the anatomical position of the appendix in the medical image based on the identified at least one pattern.

3. The method of claim 2, wherein the anatomical position of the appendix is at least one of an anterior position, a retrocecal position, a post-ileal position, a paracecal position, a posterior position, a subcecal position, a pelvic position, or a promontoric position.

4. The method of claim 1, wherein the anatomical position of the appendix is at least one of an anterior position, a retrocecal position, a post-ileal position, a paracecal position, a posterior position, a subcecal position, a pelvic position, or a promontoric position.

5. The method of claim 1, wherein the dimension of the appendix comprises one or more of a width of the appendix, a length/height of the appendix, or a diameter of the appendix.

6. The method of claim 1, wherein the pre-defined threshold associated with the appendix comprises a width of the appendix to be in a range of 3 mm to 5 mm, a height of the appendix to be in a range of 80 mm to 100 mm, and a diameter of the appendix to be in a range of 8 mm to 12 mm.

7. A computer implemented method of training a machine learning model for determining presence of appendicitis in a patient, the method comprising:
  receiving a medical image representing an appendix of the patient;
  receiving the machine learning model;
  determining, by the machine learning model, an anatomical position and dimensions associated with the appendix in the medical image, wherein the determining of the dimensions comprises: (1) analyzing the medical image to obtain pixel information associated with the appendix in the medical image; (2) identifying one or more pixel values from the pixel information associated with the appendix; (3) identifying one or more edges of the appendix based on the one or more pixel values; and (4) determining the dimension associated with the appendix from the identified one or more edges;
  comparing the determined anatomical position and the dimensions with a pre-labelled set of medical images, wherein the pre-labelled set of medical images comprise labelled information related to anatomical position of the appendix and the dimensions associated with the appendix; and
  adjusting the machine learning model based on an outcome of the comparison.

8. The method of claim 7, further comprising:
  obtaining one or more medical images associated with appendixes associated with a plurality of patients,
  wherein the one or more medical images represent multiple anatomical positions of the appendixes,
  wherein the one or more medical images comprise appendixes of different dimensions, and
  wherein the anatomical position and the dimensions associated with the appendixes are additionally determined based on the one or more medical images.

9. A medical imaging device for determining presence of appendicitis in a patient, the medical imaging device comprising:
  one or more processing units;
  a scanner unit configured to capture one or more medical images; and
  a memory coupled to the one or more processing units, the memory configured to:
    receive a medical image associated with the patient, wherein the medical image comprises an appendix of the patient;
    determine, using at least one trained machine learning model, an anatomical position of the appendix in the medical image;
    determine, using the at least one trained machine learning model, a dimension associated with the appendix in the medical image comprising: (1) analyzing the medical image to obtain pixel information associated with the appendix in the medical image; (2) identifying one or more pixel values from the pixel information associated with the appendix; (3) identifying one or more edges of the appendix based on the one or more pixel values; and (4) determining the dimension associated with the appendix from the identified one or more edges;
    identify, using the at least one trained machine learning model, if the dimension associated with the appendix is above a pre-defined threshold; and
    generate a notification on an output unit when the dimension associated with the appendix is above the pre-defined threshold,
    wherein the dimension associated with the appendix being above the pre-defined threshold indicates presence of appendicitis in the patient.

10. The medical imaging device of claim 9, wherein, in the determining of the anatomical position of the appendix, the memory is configured to:
  identify at least one pattern from the pixel information, wherein the pattern represents anatomical positional information associated with the appendix; and
  determine the anatomical position of the appendix in the medical image based on the identified at least one pattern.

11. A system for determining a presence of appendicitis in a patient, the system comprising:
  one or more servers;
  a medical imaging unit coupled to the one or more servers;
  the one or more servers comprising instructions, which when executed causes the one or more servers to:
    receive a medical image associated with the patient, wherein the medical image comprises an appendix of the patient;
    determine, using at least one trained machine learning model, an anatomical position of the appendix in the medical image;
    determine, using the at least one trained machine learning model, a dimension associated with the appendix in the medical image comprising: (1) analyzing the medical image to obtain pixel information associated with the appendix in the medical image; (2) identifying one or more pixel values from the pixel information associated with the appendix; (3) identifying one or more edges of the appendix based on the one or more pixel values; and (4) determining the dimension associated with the appendix from the identified one or more edges;
    identify, using the at least one trained machine learning model, if the dimension associated with the appendix is above a pre-defined threshold; and
    generate a notification on an output unit when the dimension associated with the appendix is above the pre-defined threshold,
    wherein the dimension associated with the appendix being above the pre-defined threshold indicates presence of appendicitis in the patient.

12. The system of claim 11, in the determining of the anatomical position of the appendix, the instructions cause the one or more servers to:
  identify at least one pattern from the pixel information, wherein the pattern represents anatomical positional information associated with the appendix; and
  determine the anatomical position of the appendix in the medical image based on the identified at least one pattern.

13. A non-transitory computer readable storage medium storing machine-readable instructions therein, that when executed by a processor, causes the processor to:

receive a medical image associated with a patient, wherein the medical image comprises an appendix of the patient;

determine, using at least one trained machine learning model, an anatomical position of the appendix in the medical image;

determine, using the at least one trained machine learning model, a dimension associated with the appendix in the medical image comprising: (1) analyzing the medical image to obtain pixel information associated with the appendix in the medical image; (2) identifying one or more pixel values from the pixel information associated with the appendix: (3) identifying one or more edges of the appendix based on the one or more pixel values; and (4) determining the dimension associated with the appendix from the identified one or more edges;

identify, using the at least one trained machine learning model, if the dimension associated with the appendix is above a pre-defined threshold; and generate a notification on an output unit when the dimension associated with the appendix is above the pre-defined threshold, wherein the dimension associated with the appendix being above the pre-defined threshold indicates presence of appendicitis in the patient.

* * * * *